(12) United States Patent
Sillerud

(10) Patent No.: US 9,110,067 B2
(45) Date of Patent: *Aug. 18, 2015

(54) MAGNECYTOMETER FOR THE DETECTION OF ONE OR MORE ANALYTES

(71) Applicant: STC.UNM, Albuquerque, NM (US)

(72) Inventor: Laurel Sillerud, Albuquerque, NM (US)

(73) Assignee: The Regents of the University of New Mexico, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/213,301

(22) Filed: Mar. 14, 2014

(65) Prior Publication Data

US 2014/0273005 A1 Sep. 18, 2014

Related U.S. Application Data

(60) Provisional application No. 61/785,508, filed on Mar. 14, 2013.

(51) Int. Cl.
| | |
|---|---|
| *G01N 24/08* | (2006.01) |
| *G01N 33/574* | (2006.01) |
| *G01N 33/543* | (2006.01) |
| *G01R 33/30* | (2006.01) |

(52) U.S. Cl.
CPC .......... *G01N 33/57438* (2013.01); *G01N 24/08* (2013.01); *G01N 33/54306* (2013.01); *G01N 33/574* (2013.01); *G01R 33/307* (2013.01)

(58) Field of Classification Search
None
See application file for complete search history.

(56) References Cited

U.S. PATENT DOCUMENTS

| | | | | |
|---|---|---|---|---|
| 7,829,350 | B2 * | 11/2010 | Josephson et al. | 436/526 |
| 8,821,868 | B2 * | 9/2014 | Goldenberg et al. | 424/130.1 |
| 2013/0281324 | A1 * | 10/2013 | Gouliaev et al. | 506/26 |

OTHER PUBLICATIONS

Williams et al. (Technical Advanced Description 2006 total 4 pages).*

* cited by examiner

*Primary Examiner* — Jacob Cheu
(74) *Attorney, Agent, or Firm* — Keith A. Vogt; Vogt IP

(57) ABSTRACT

A system and method for analyzing a sample of liquid having an NMR signal in response to a magnetic field for the presence of an analyte. Included is an NMR device having a testing section that is adapted to contain a liquid and apply a magnetic field to the liquid. A complex comprised of a conjugate having a field gradient bound to the analyte that is of sufficient magnitude to quench the NMR signal of the liquid when in the test section whereby the presence of the complex is determined by the absence of the NMR signal.

20 Claims, 8 Drawing Sheets

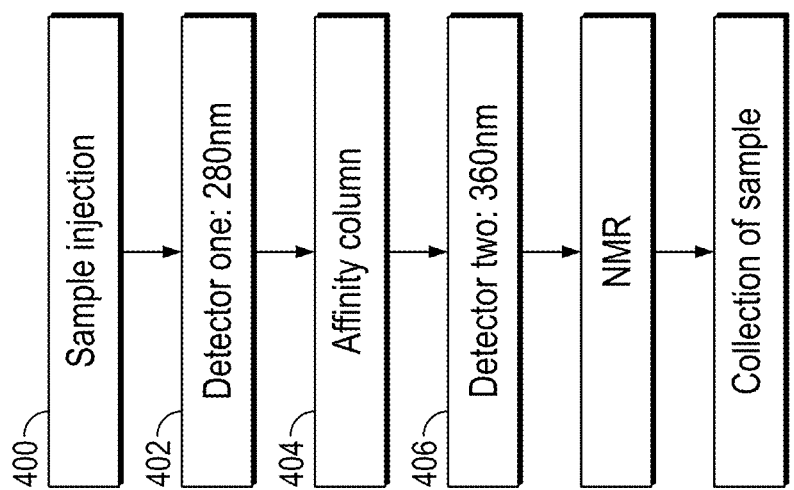
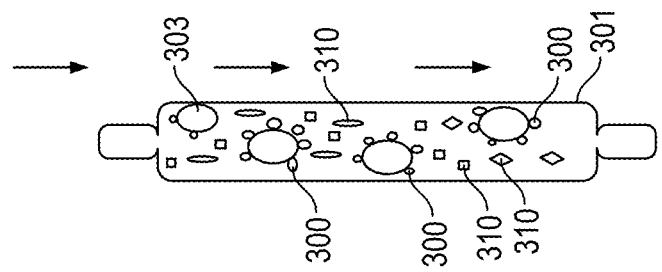

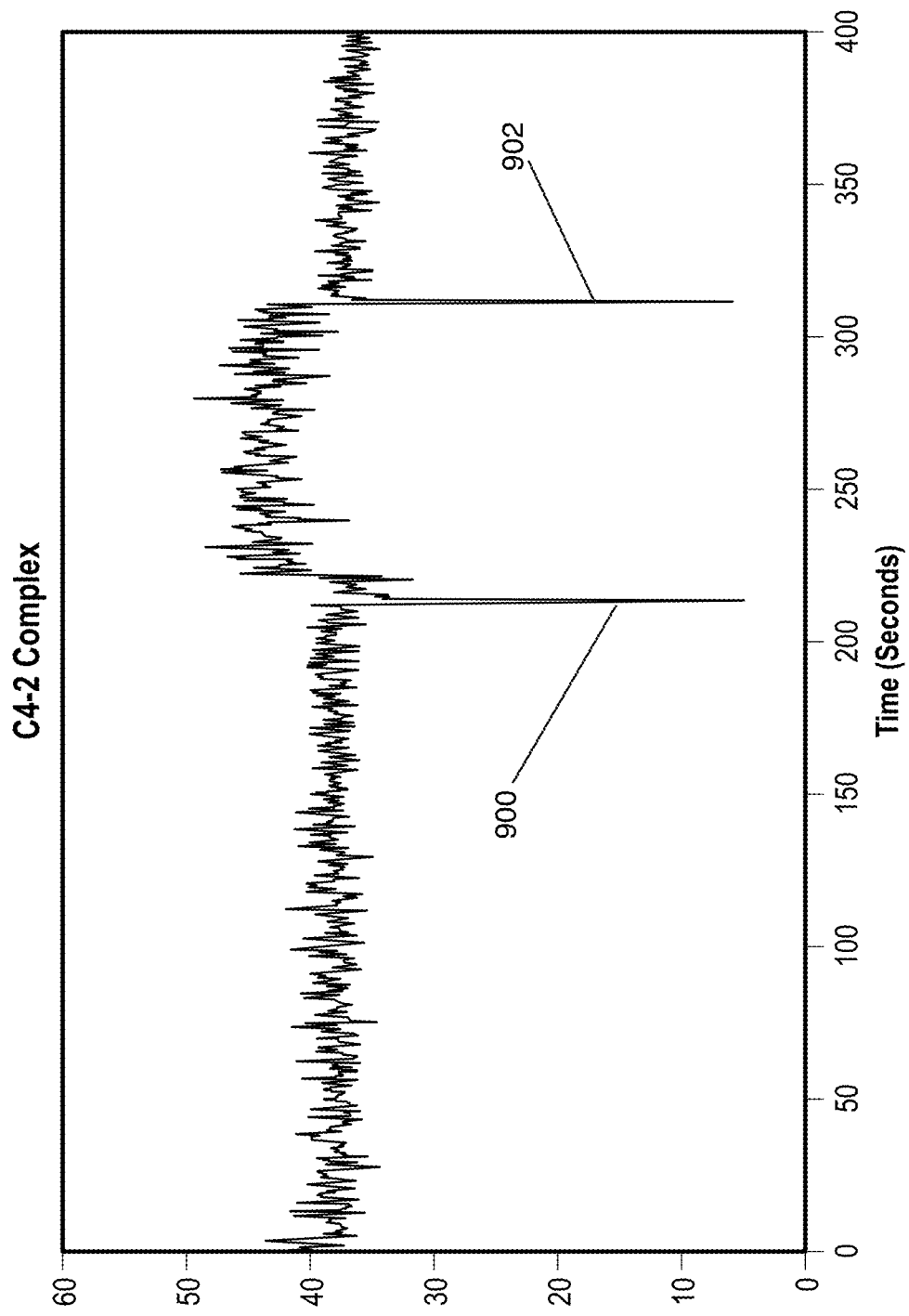

US 9,110,067 B2

MAGNECYTOMETER FOR THE DETECTION OF ONE OR MORE ANALYTES

CROSS-REFERENCE TO RELATED APPLICATIONS

This application claims the benefit U.S. Provisional Application No. 61/785,508, filed Mar. 14, 2013 and herein incorporated by reference.

STATEMENT REGARDING FEDERALLY SPONSORED RESEARCH OR DEVELOPMENT

Not Applicable.

INCORPORATION-BY-REFERENCE OF MATERIAL SUBMITTED ON A COMPACT DISC

Not Applicable.

BACKGROUND OF THE INVENTION

1. Field of the Invention

There is a need for efficient, inexpensive diagnostic tools that may be used in the detection of diseases in patients. A cost-effective diagnostic system that delivers timely results would enhance point of care analyses and ultimately save lives.

2. Brief Summary of the Invention

The present invention avoids the general drawbacks of the prior art by using nuclear magnetic resonance (NMR) spectroscopy that has the sensitivity to detect single magnetic nanoparticles in an aqueous solution. In one embodiment, the present invention provides a novel NMR microcoil spectroscopic flow cytometer (a Magnecytometer), which performs ultra-sensitive cell detection and isolation. The invention uses the technique of binding of antibody-conjugated, super-paramagnetic iron oxide nanoparticles (SPIONs) to tumor cells or other cells of interest and flow NMR spectroscopy of water in the surrounding buffer solution. The invention utilizes the SPION-induced alteration in the NMR relaxation of the water in an NMR microcoil as a detection mechanism. The invention has the sensitivity to detect a single cell obtained from a small volume of liquid. The invention may also be applied to the detection and capture of almost any type of cell, virus or macromolecule.

BRIEF DESCRIPTION OF THE SEVERAL VIEWS OF THE DRAWINGS

FIG. 3 is a schematic of another embodiment of the invention.

FIG. 4 is a flowchart of an embodiment of the invention.

FIG. 9 is a graph showing the continuous NMR spectrum of a complex with C4-2 cells. Approximately 5 cells were detected.

DETAILED DESCRIPTION OF THE INVENTION

Figure 1:
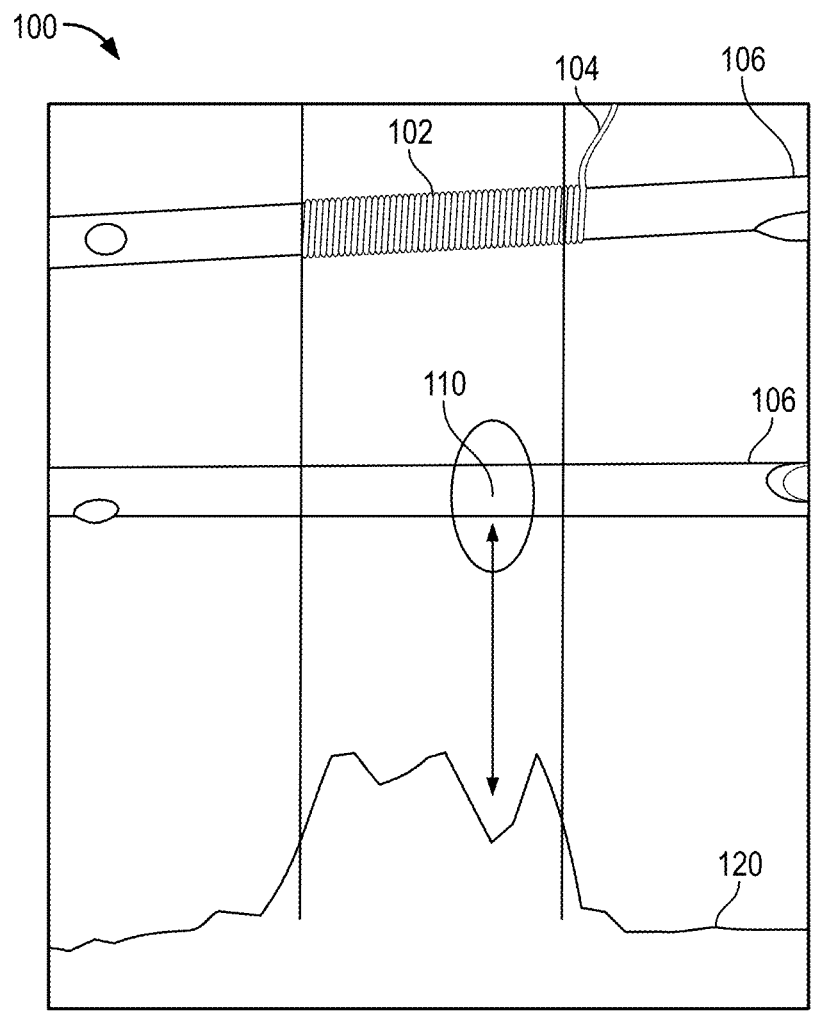
FIG. 1 is a schematic of an embodiment of the invention.

This description is not to be taken a limiting sense, but is made merely for the purpose of illustrating the general principles of the invention. The scope of the invention is defined by the appended claims. In a preferred embodiment, the present invention provides a device and method for analyzing a sample of liquid having an NMR signal in response to a magnetic field for the presence of an analyte. As shown in FIG. 1, an analyte 110 such as a single cell, a cancer cell or even a single cancer cell, is located in a nuclear magnetic resonance device 100 having a sample testing section 102, which may be 1 microliter or less in volume, in which a magnetic field is applied by coil 104 that surrounds tube 106. Analyte 110 may be conjugated with a conjugate, which may be paramagnetic or superparamagnetic, having a field gradient that quenches all or sonic of the NMR signal of the liquid in the sample testing section 102. Testing is performed by applying a magnetic field when a liquid containing a potential analyte is located in sample testing section 102 to determine the presence of the analyte 110 based upon the NMR signal 120 of the liquid being quenched by the conjugate.

For detecting a single bead in the device shown in FIG. 1, a bead was placed in agarose under high temperature conditions. The temperature was then lowered to fix the bead in place inside capillary tube. A coil was then wrapped around the capillary and NMR was performed.

Figure 2:
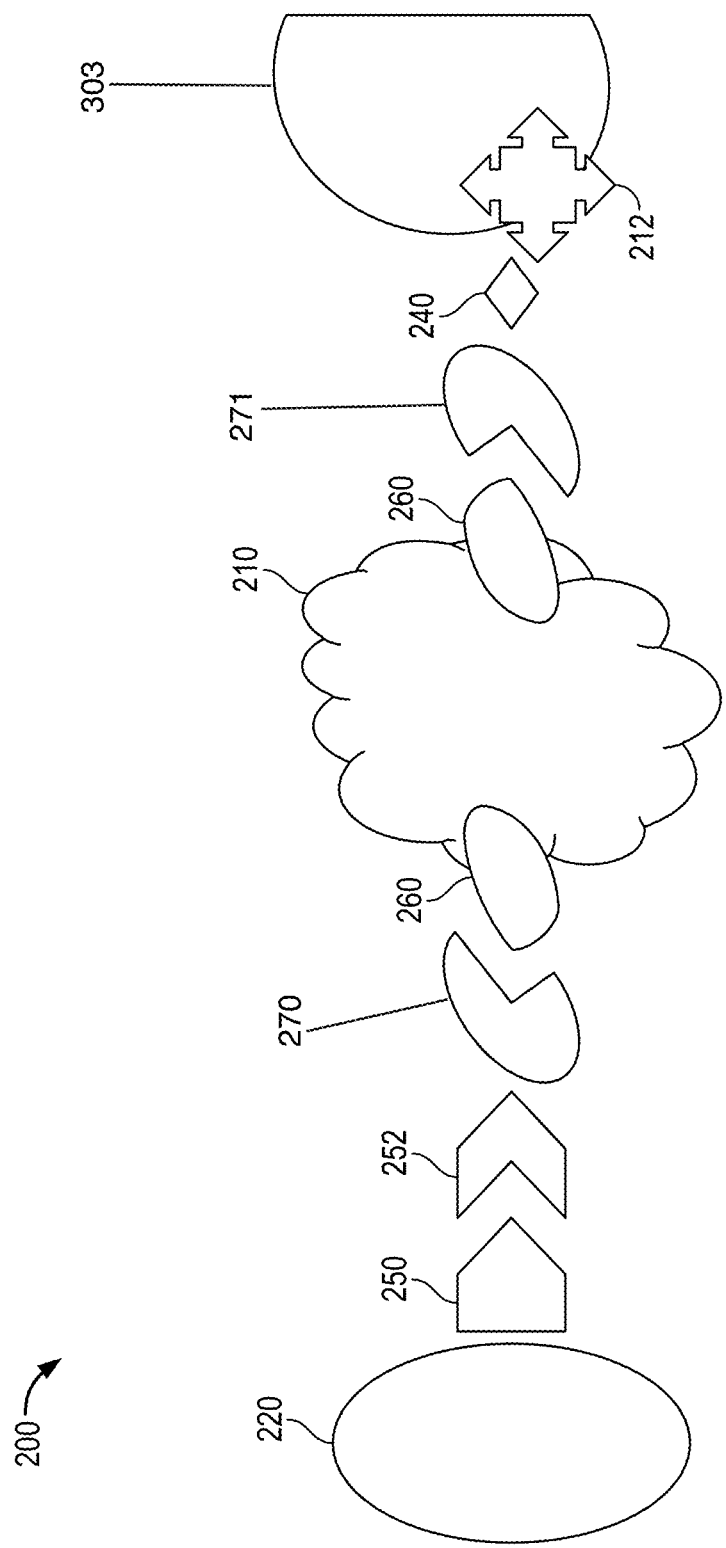
FIG. 2 illustrates a biological complex that may be used with the invention.

To test a small sample size of liquid, another embodiment of the invention prepares the analyte for analysis by creating a biological complex 200 as show in FIG. 2. The biological complex is comprised of a recognition ligand 212 bound to the analyte 210. The recognition ligand 212 has an affinity to the analyte and an affinity to an affinity column resulting in the attachment of the biological complex to the affinity column. This permits the conjugate 220 to bind with the analyte and also creates an elution solution for analysis when the biological complex is removed from the column. A biological marker 240 may also be attached to the analyte 210 for testing of the presence of the analyte prior to attaching the analyte to an affinity column. Moreover, to concentrate the analyte, the presence of the biological marker is also tested as the analyte passes through the affinity column with the process continuing until no analyte is detected passing through the column. After testing, a magnet may be used to remove the biological complexes from the elution solution.

For a complex formed in the column using a prostate cancer cell, the Nickel agarose bead non-covalently binds the His-Tagged antibody that is attached to a chromophore. The Antibody is then attached to the prostate cancer cell via the receptor PSMA. SPIONs are then attached to the cell via a streptavidin-biotinylated anti-PSMA 270 and 271.

The above-described embodiment uses a nuclear magnetic resonance (NMR) based flow cytometer (a Magnecytometer) to provide a rapid, specific detection of small numbers of biological objects, such as cells, proteins, and viruses in native biological fluids without the need for preprocessing or separations. Since biochemistry is chemistry which takes place in water, the invention uses the NMR spectroscopic signal from the abundant (~111 Molar) solvent water protons to produce a large NMR signal. The detection scheme relies on the modification of a water signal in the presence of a conjugate that acts as a signal modifier, such as super-paramagnetic iron oxide nanoparticles (SPIONs). SPIONs possess no intrinsic magnetic field, but when placed into the static field of an NMR magnet, they become magnetically-saturated and produce magnetic field gradients which extend radially up to 50 micrometers. Water protons diffusing in these strong gradients experience decreased transverse relaxation times with subsequent line broadening. Using this property of SPIONs it can be shown that a single 1 micrometer SPION would perturb the NMR signal from ~0.5 nL of the surrounding water containing an easily-detectable ~$10^{17}$ protons.

Accordingly, by matching the volume of liquid in test section 102 with a conjugate having a field gradient that quenches the NMR signal of the liquid in the test section 102 a single analyte may be detected. In a specific embodiment, matching an 80 micrometer diameter NMR microcoil having a testing section containing this volume of water with a single SPION conjugate will quench the NMR signal from the water in this volume. SPIONs can also be conjugated to molecules, such as antibodies, that recognize other biological molecules. Therefore, attaching a conjugated SPIONs to biological analytes, and separate analyte-bound SPIONs from those lacking bound analytes, the microcoil NMR 100 may be used to detect conjugates, such as SPIONs, acting as surrogates, or signal amplifiers, for cells, viruses or molecules that are associated with a variety of diseases. Signal modifiers such as SPIONs may be attached as conjugates to antibodies directed against cell receptors and then may be used for single cell detection.

Another aspect of the invention is a method for ensuring that only those conjugates that have bound to an analyte pass through the NMR microcoil for counting. Another aspect of the invention addresses the fact that biological objects of interest are often dilute, so that large fluid volumes would need to be processed or examined. The passage of large volumes (1-100 mL) of fluid through an NMR microcoil would require inconveniently-large amounts of time.

The present invention addresses both these considerations with the aid of affinity column chromatography as shown in FIG. 3 which allows a biological complex 300, as described above, to be assembled in a step-wise fashion on column 301, by washing off the unbound, and non-specific material 310, and only eluting the conjugate or SPION-bound complex 300 that is passed through the NMR device 100.

During the assembly of the complex, the analyte may be concentrated by processing arbitrary amounts of fluid. The analyte may also be recovered with a magnet after it has passed through the NMR microcoil for later use because the analyte would be now attached to magnetic beads 220. In this manner it is possible to use antibodies 212 as recognition ligands for single cell detection even in large amounts of biological fluids.

Possible uses for the invention include, but are not limited to, measuring circulating tumor cells in blood. The large number of unwanted erythrocytes and other blood cells would constitute a non-interfering background. It is also important to note than magnecytometry is minimally invasive, requiring only a small amount of blood of approximately 30 microliters. Thus, the invention may improve the way doctors diagnose diseases such as prostate cancer which often metastasizes and therefore circulating tumor cells can be found in the blood, even in early stages of the disease.

In one preferred embodiment, the affinity column 301 may be packed with nickel (Ni)-agarose 303, then a His-tagged antibody 212 is run through the system and recycled to fully saturate the nickel agarose column. The next step is to run a sample through the column and wash with a 2.5 mM imidazole (Sigma™, St. Louis, Mo.) wash buffer, this ensures there are no containments other than the analyte 210 of interest attached to the column that will decrease the chance of a false positive running through the NMR.

As shown in FIG. 4, two spectrophotometers 402 and 406 on either side of the column may also be used. The first detector 402 detects proteins going into column 301. The second detector 406 detects for a biological marker such as a chromophore 240 that is attached to the His-tagged antibody 212. The His-tagged antibody attaches to the Ni-agarose column for the direct quantification of His-Tagged antibody that elutes from the column that is then released by the imidazole competitively binding to the Ni-agarose. The conjugates 220, which may be SPIONs, are then run through the column which bind via a streptavidin 250 conjugated SPIONs and a biotinylated antibody 252 that then attaches to cells of interest completing biological complex 200 as shown in FIG. 2.

Once bound, the sample is eluted with a 200 mM imidazole elution buffer to cleave the His-tagged antibodies off the column that then run through the NMR. The properties of SPION may then be used to detect for the analytes or cells of interest. Samples from the NMR may also be gathered in a fraction collector for further analysis such as determination of the protein concentration, and iron assays by using a magnet.

The NMR was Bruker™ (Madison, Wis.) MiniSpec and the solenoid coil was developed using 50 gauge copper wire wound around the outer diameter of a glass capillary tube 106 (O.D. 170 μm; I.D. 100 μm). The π/2 pulse length for this coil is 80 μs. The resonance frequency is 40.015 MHz, and contains a 100 cm permanent magnet (MRT Inc. Tsukuba Japan), all data was collected using a Hewitt Packard Windows XP™ Running Magritek (Welington, New Zealand) Prospa™, and WinDaq™ (collects optical data from detectors) on one hard drive. Data was collected via a Magritek Kea and then stored to the console. A continuous pulse repeat macro was written with the following stipulations: The macro repeats a RF pulse every 0.861 seconds for a continuous reading on each coil volume. A macro was also written to integrate the FID data for every RF pulse and generate a plot.

The nickel agarose was obtained from Thermo Scientific™ and contains 6% beaded agarose with a binding capacity of 10 mg/mL. Anti-PSMA, clone J591 antibody was purchased from Neil H. Bander, MD (Cornell College of Medicine, USA). Proteins were His-Tagged using the Solulink™ procedure and reagents. The J-591 were biotinylated using the Lightning Link™ Biotin conjugation kit Type A from Innova Bioscience. The SPIONs are manufactured by MagSense™ and are streptavidin modified. The were conjugated with biotinylated anti-PSMA antibody J591 at a ratio of $75 \times 10^3$ beads per ng antibody; Typically 200 ng J591 antibody were incubated in 0.5 mL PBS (Phosphate Buffered Saline) containing $15 \times 10^6$ beads by gentle end-over-end rotation at room temperature. Antibody-functionalized SPIONs were then combined with prostate tumor cells in PBS at a ratio of 300 beads per cell.

For an embodiment in which prostate cancer cells were detected using the invention, the PSMA receptor 260 was selected as a preferential target for SPION labeling and attaching the His-tags. The antibody for PSMA and the protein complex BSA had a His-tag placed upon them along with the hydrazonechromophore following the manufacturer's (Solulink™) procedure: The protein must first be desalted using Zeba (Thermo Scientific™, Rockford, Ill.) desalt columns. Protein concentration determination was also performed using Pierce™ Micro HCA Kit. S-4FB (linker containing chromophore) was subsequently added, using 2 mole equivalents of S-4FB per protein. The protein then was desalted using Zeba desalting columns, and protein concentration was then determined. The molar substitution ratio was subsequently determined based on the amount of protein. Protein conjugated to S-4FB was then conjugated to 6× His-Tag and was incubated at room temperature for 16 hours. Removal of excess His-tags was performed using MicroconUltracelYM-3 spin column with a 3000 molecular weight cut-off. The biological complex was then washed twice with PBS and concentration of protein complex determined, and labeling was determined using absorbance at 360 nm. The antibodies were also conjugated to biotin, using the Lightning Link™ Biotin conjugation Kit from Innova Biosciences. Protein concentration determination was done prior to biotinylation, then 1 µL of LL-modifier reagent was added for every 10 µL of antibody used. This mixture was then added to Lightning Link™ mix and resuspended resulting in a mixture that was then incubated for 3 hours at room temperature and 1 µL of LL-quencher was added for every 10 µL of antibody used. Protein concentration was again determined.

The C4-2 prostate cancer cell line that was grown in vented cell culture flasks (BD Biosciences, San Jose, Calif.) in Dulbecco's modified Eagle's media (DMEM) containing: 4.5 g/L glucose and 2 mM L-glutamine (Sigma™, St. Louis, Mo.), and supplemented with 10% fetal bovine serum (FBS; Hyclone, Logan Utah) and penicillin/streptomycin at 100 U (Sigma™). The cells were grown at 37° C. in a humidified 95% $O_2$/5% $CO_2$ atmosphere to passage numbers typically not exceeding 35 to avoid genotypic drifts; Cell detachment was in 0.5% trypsin containing 0.02% EDTA (Sigma™) for 30 seconds upon reaching 60-80% confluence; Trypsin action was stopped by adding medium and cells were harvested by centrifugation at 150×g for 10 minutes at room temperature, then resuspended in phosphate buffered saline (PBS; Sigma™). Cell numbers were counted using a hemocytometer.

FIG. 4 illustrates an exemplary process flow of an embodiment of the invention. As shown, sample 400 is injected and data is acquired by detector 402, which may be set at 280 nm or any other suitable wavelength, and stored by a processor. The sample then flows through affinity column 404 where a desired protein binds to the His-tagged antibody specific for the cell or protein of interest and the remainder of the sample flows past detector 406 and can be recycled through the column to ensure maximum binding. Then the wash buffer containing 2.5 mM imidazole flows through the system releasing excess particles and molecules not bound to column. Elution buffer containing a high concentration (200 mM) of imidazole then releases His-Tagged antibodies bound to the column, also releasing cells/proteins of interest bound to SPIONs.

Detector 406 may be set at 360 nm, or any other suitable wavelength, detects the chromophore 240 attached to His-Tagged antibodies 212 that run through the NMR. Small quantities of SPIONs 220 can therefore be detected. The embodiment may be used to process small quantities of cells labeled with magnetic beads 220 (~5 cells) for detection.

Figure 5:
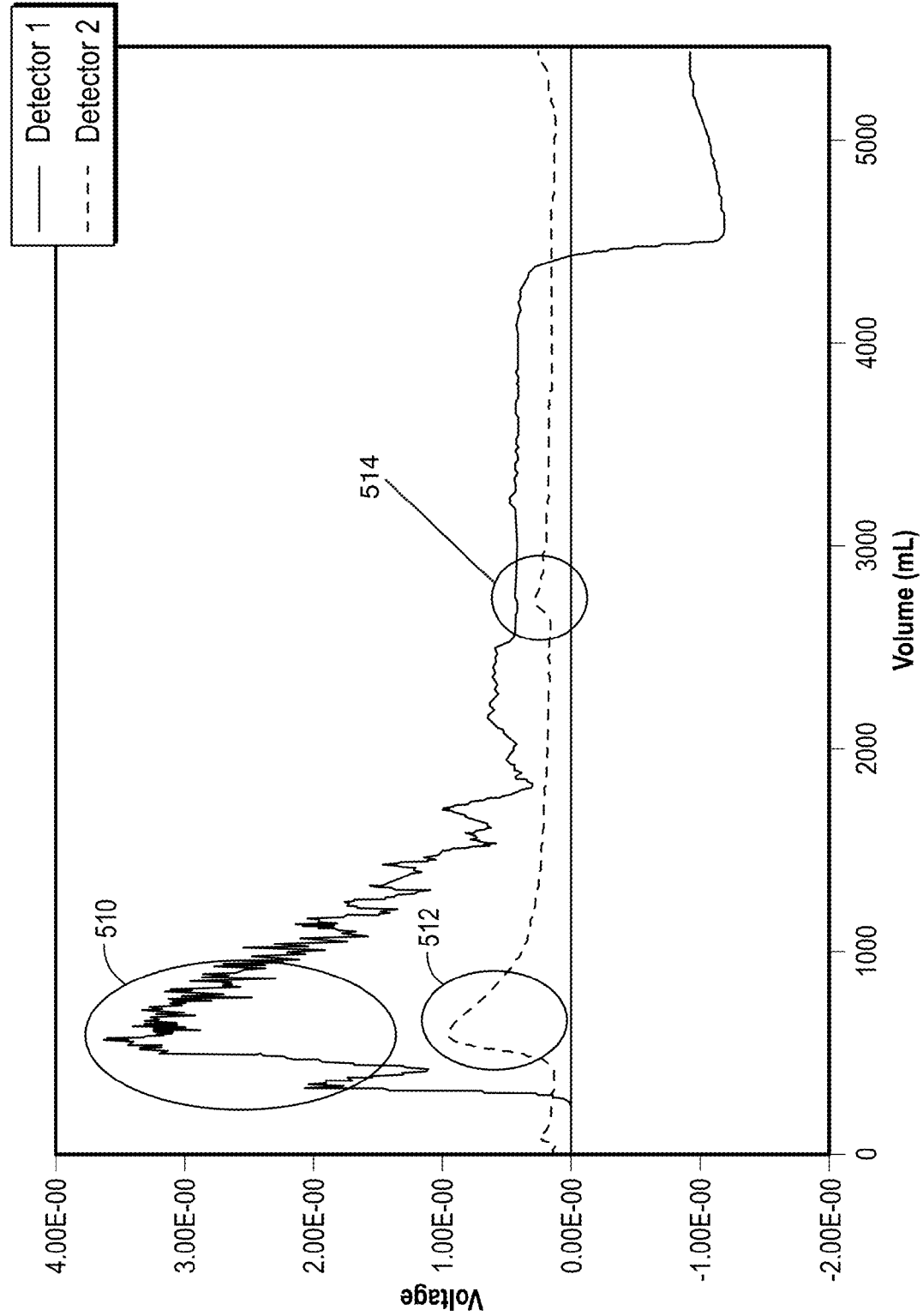
FIG. 5 is a graph showing volume dependent loading and washing profiles of His-tagged BSA-SPION complex. The first D1 peak shows the amount of protein entering the column. The first D2 peak shows protein exiting the column. The second peak of D2 gives the washing profile.

Continuing to pass analytes past detector 406 until no reading or a sufficiently low reading is obtained. This reduces false positives from occurring as shown in FIG. 5. A spectrophotometer functions as a detector was placed before the affinity column to detects the amounts of protein prior to entering the column as described above. For an example used in accordance with the present invention, FIG. 5 shows that 368.11 mg/mL of protein entered the column as shown by peak 510 for detector 402 and 56.458 mg/mL of His-Tagged protein exited the column as demonstrated by peak 512 for detector 406. Peak 510 shows protein entering the column. Peak 512 shows protein exiting the column. Peak 514 shows the wash buffer releasing unbound SPIONs and gives the washing profile.

As further shown in FIG. 1, a single biological complex 200 identified as number 110 was placed in test chamber or section 102 of device 100. NMR was then performed showing the quenched water proton signal 120 indicating the presence of the analyte of interest. The detection of a single bead in the test chamber may then be used to count the number of analytes present as an elution solution flows through the device.

Figure 6B:
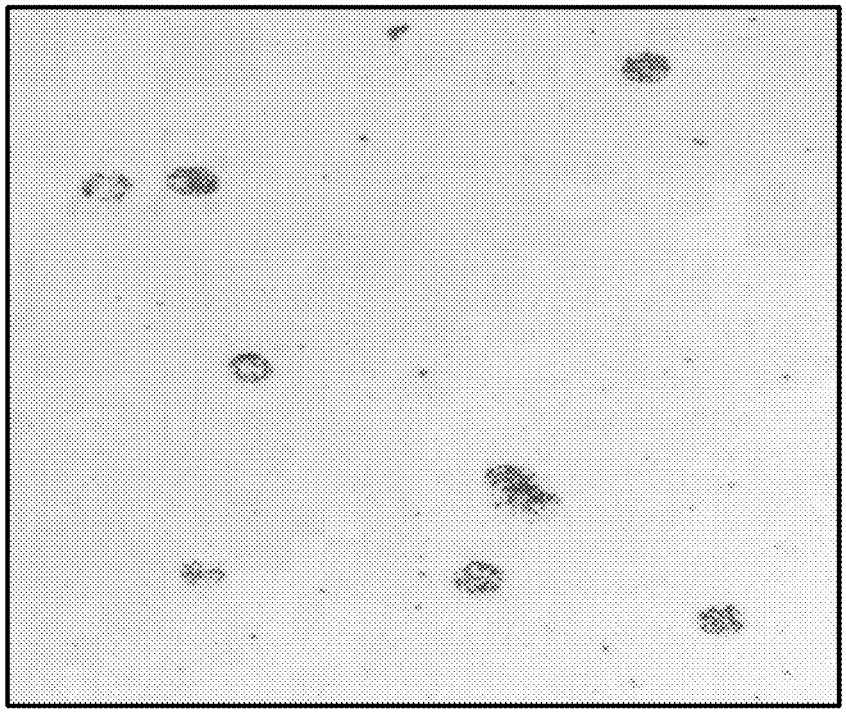
FIGS. 6A and 6B illustrate how SPIONs quench a magnetic signal of a liquid.
Figure 6A:
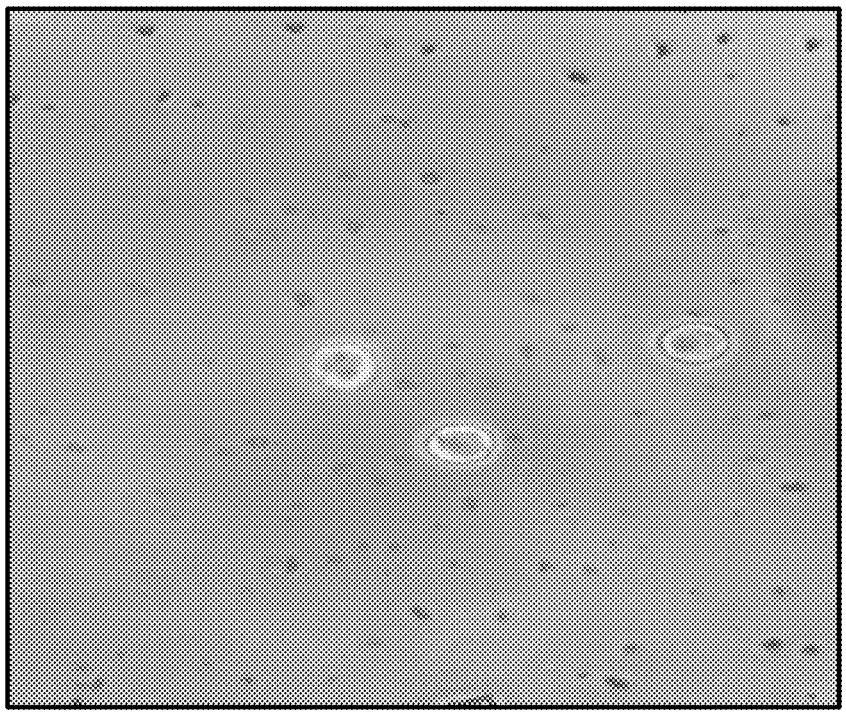

FIGS. 6A and 6B illustrate the effect on water protons when stimulated by SPIONs at varying concentration of magnetic beads. FIG. 6A shows cells that do not express PSMA and therefore are not magnetically labeled with SPIONs. FIG. 6B shows cells that overexpress PSMA and bind SPIONs.

Figure 7:
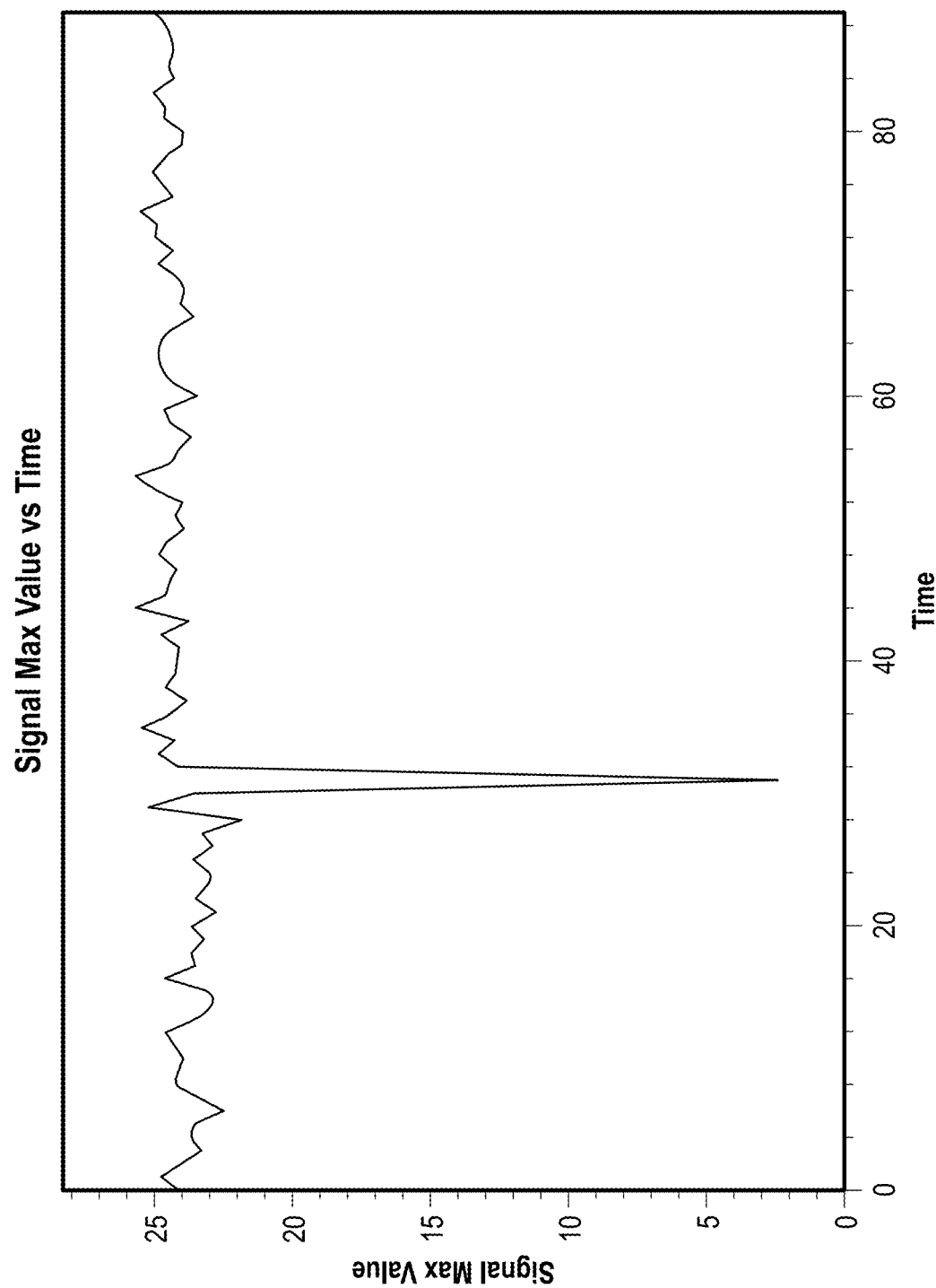
FIG. 7 is a graph showing the NMR continuous spectra of BSA complex. Approximately 250 beads were detected.
Figure 8:
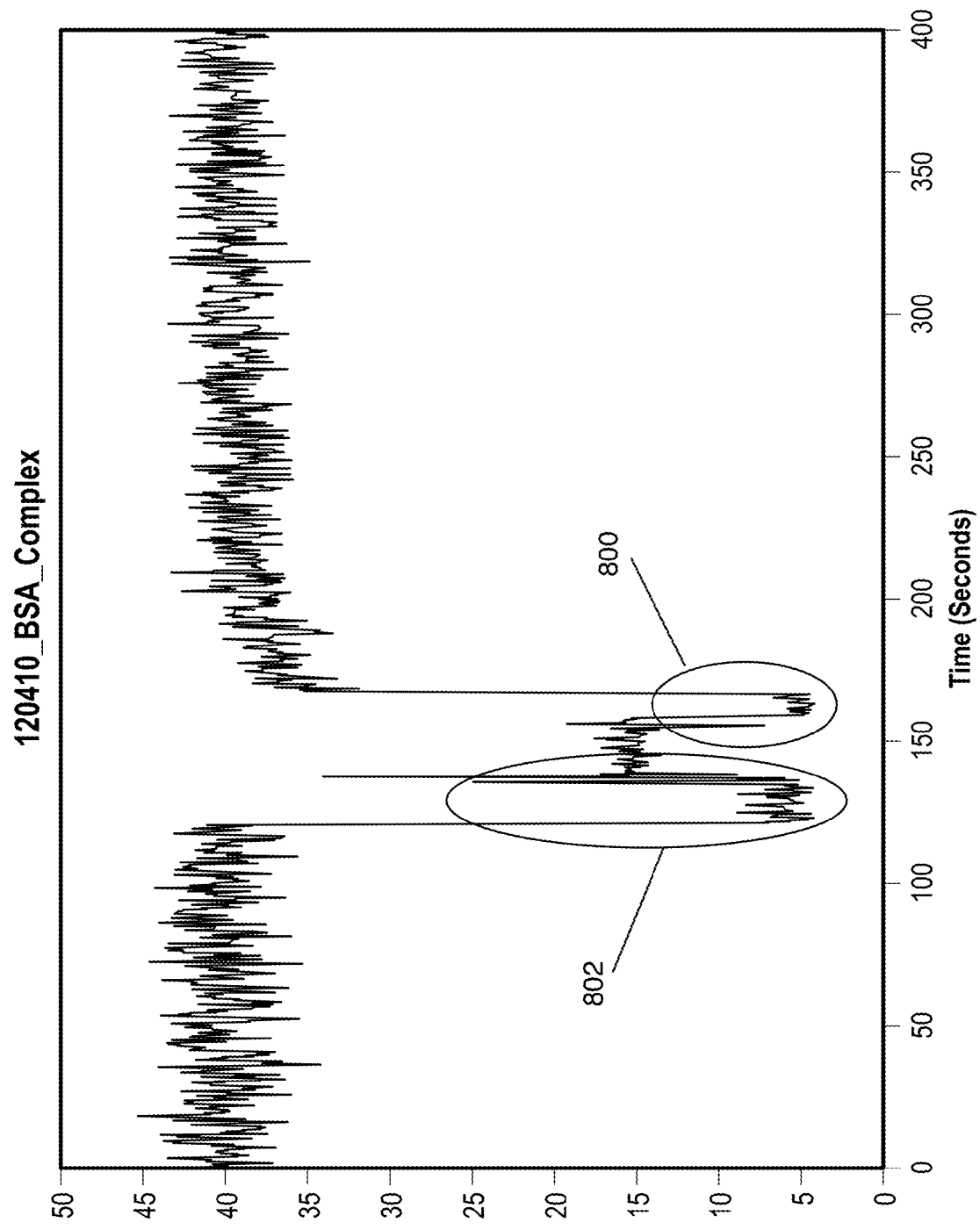
FIG. 8 is a graph showing the continuous NMR spectrum of complete complex using BSA.1.6E6 molecules detected.

FIG. 7 illustrates the continuous NMR spectrum of the water protons being quenched by the BSA complex. An after iron assay was performed and it was determined that 3.6E6 beads and 1.8E6 BSA molecules (BSA binds two beads per molecule) were bound and eluted from the column. FIGS. 8 and 9 are the NMR continuous spectra of C4-2 prostate cancer cells, which over express PSMA. The data shows that the cells were successfully bound to the column and detected using NMR. It was determined that approximately 5 cells were detected and characterized. Portion 800 shows the His-Tagged attached to the protein of interest. Portion 802 shows the wash removing the unbound SPIONs. Portion 902 shows C4-2 cells. Portion 900 shows the wash removing the unbound SPIONs.

What is claimed is:

1. A method for analyzing a sample of liquid having an NMR signal in response to a magnetic field for the presence of a single analyte, the method comprising the steps of:
   conjugating said single analyte with a conjugate, said conjugate having a field gradient that quenches the NMR signal of the liquid;
   placing said single analyte in a sample testing section of a nuclear magnetic resonance device, said sample test section sized to receive a single analyte and to contain a volume of liquid such that said field gradient of said conjugate quenches the NMR signal of the liquid in said sample testing section;
   applying a magnetic field to said single analyte when said single analyte is located in said sample testing section; and
   determining the presence of said single analyte based upon said conjugate quenching the NMR signal of the liquid in said sample testing section.

2. The method of claim 1 wherein said analyte is a single cell.

3. The method of claim 1 wherein said analyte is a single cancer cell.

4. The method of claim 1 wherein said conjugate is paramagnetic or superparamagnetic.

5. The method of claim 1 wherein said sample testing section is sized to contain a volume of liquid such that said field gradient of said conjugate of said single analyte quenches the entire NMR signal of the liquid in said sample testing section.

6. The method of claim 1 wherein said sample test section has a volume of 1 microliter or less.

7. The method of claim 1 further comprising the steps of preparing said analyte for analysis comprising the steps of:
   creating a biological complex comprised of a recognition ligand bound to said analyte by providing a recognition ligand that has an affinity to said analyte and an affinity column;

attaching said biological complex to said affinity column; and conjugating said conjugate to said analyte and creating an elution solution for analysis by removing said biological complex from said column.

8. The method of claim 7 further comprising the steps of:
attaching a biological marker to said analyte;
testing for said biological marker prior to attaching to said analyte to said affinity column;
testing for said biological marker after said analyte passes through said affinity column; and
continuing to pass said analyte through said column until no analyte is detected passing through the column.

9. A method for using a nuclear magnetic resonance device to count one or more analytes one-at-a-time in a sample liquid having an NMR signal in response to a magnetic field comprising the steps of:
attaching a biological marker to said analytes;
testing for said biological marker prior to attaching said analytes to an affinity column;
testing for said biological marker after said one or more analytes pass through said affinity column;
continuing to pass said one or more analytes through said column until no analytes are detected passing through the column to create an elution solution;
said elution solution containing one or more biological complexes comprised of analytes bound to recognition ligands, said biological complexes formed by conjugating a conjugate to said one or more analytes, said conjugate having a field gradient that quenches the NMR signal of the liquid;
attaching said one or more biological complexes to said affinity column;
passing said elution solution through a nuclear magnetic resonance device having a sample testing section in which a magnetic field is applied, said sample test section is sized to receive a single biological complex and to contain a volume of liquid such that said field gradient of said conjugate of said single biological complex quenches the entire NMR signal of the liquid in said sample testing section;
applying a magnetic field to said single biological complex when said biological complex is located in said sample testing section; and counting said biological complexes one-at-a-time by determining the presence of a biological complex based upon said NMR signal from the liquid being entirely quenched by said conjugate.

10. The method of claim 9 wherein a magnet is used to remove said biological complexes from said elution solution.

11. The method of claim 9 wherein said analyte is a single cancer cell.

12. The method of claim 9 wherein said conjugate is paramagnetic or superparamagnetic.

13. The method of claim 9 wherein said sample test section has a volume of 1 microliter or less.

14. The method of claim 3 wherein said analyte is a single pancreatic cancer cell.

15. The method of claim 11 wherein said analyte is a single pancreatic cancer cell.

16. A method for analyzing a sample of liquid having an NMR signal in response to a magnetic field for the presence of an analyte, the method comprising the steps of:
conjugating said analyte with a conjugate, said conjugate having a field gradient that quenches the NMR signal of the liquid;
placing said analyte in a sample testing section of a nuclear magnetic resonance device, said sample test section is sized to contain a volume of liquid such that said field gradient of said conjugate quenches the entire NMR signal of the liquid in said sample testing section;
applying a magnetic field to said analyte when said analyte is located in said sample testing section; and
determining the presence of said analyte based upon said conjugate quenching the entire NMR signal of the liquid in said sample testing section.

17. The method of claim 16 wherein said analyte is a single cell.

18. The method of claim 1 wherein said analyte is a single cancer cell.

19. The method of claim 16 wherein said sample testing section has a volume of 1 microliter or less.

20. The method of claim 16 wherein said sample testing section is sized to only receive a single analyte.

* * * * *